United States Patent [19]

Mieville

[11] 4,233,298
[45] Nov. 11, 1980

[54] ESTERS OF P-CARBONYLPHENOXY-ISOBUTYRIC ACIDS

[75] Inventor: Andre Mieville, Lausanne, Switzerland

[73] Assignee: Orchimed SA, Switzerland

[21] Appl. No.: 829,964

[22] Filed: Sep. 1, 1977

Related U.S. Application Data

[60] Division of Ser. No. 600,127, Jul. 29, 1975, Pat. No. 4,058,552, which is a continuation-in-part of Ser. No. 326,188, Jan. 24, 1973, Pat. No. 3,907,792, which is a continuation-in-part of Ser. No. 8,071, Feb. 2, 1970, Pat. No. 3,914,286.

[30] Foreign Application Priority Data

Jan. 31, 1969 [CH] Switzerland ............... 1517/69
Aug. 28, 1969 [CH] Switzerland ............. 13022/69

[51] Int. Cl.³ ............... C07C 93/20; C07C 147/07; C07C 149/43; C07D 295/14
[52] U.S. Cl. .................. 424/244; 260/239 BF; 260/326.43; 424/248.5; 424/248.52; 424/248.55; 424/267; 424/274; 424/308; 544/158; 544/171; 546/238; 546/239; 560/9; 560/11; 560/52; 560/53
[58] Field of Search ............ 260/239 BF, 326.43; 560/9, 11, 17, 52, 53; 546/238, 239; 544/158, 171; 424/244, 248.5, 248.55, 267, 274, 308

[56] References Cited

U.S. PATENT DOCUMENTS

| | | | |
|---|---|---|---|
| 3,828,093 | 8/1974 | Bays et al. | 560/52 |
| 3,880,916 | 4/1975 | Dickel et al. | 560/52 |
| 3,914,286 | 10/1975 | Mieville | 560/53 |

FOREIGN PATENT DOCUMENTS

2003430 9/1970 Fed. Rep. of Germany ............. 560/53

*Primary Examiner*—Alton D. Rollins
*Attorney, Agent, or Firm*—Robert E. Burns; Emmanuel J. Lobato; Bruce L. Adams

[57] ABSTRACT

This invention is concerned with esters of p-carbonylphenoxy-isobutyric acids of the general formulae:

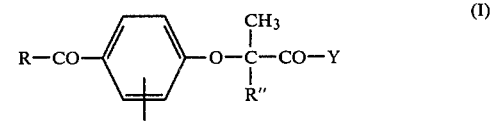

(I)

and

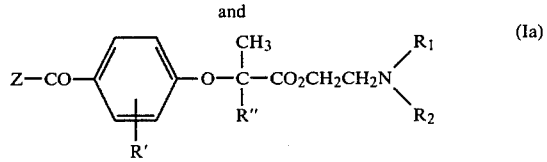

(Ia)

wherein
R is a phenyl group substituted by one or two halogen atoms;
R' is H, $CH_3$, $C_6H_5$, $SCH_3$, $OCH_3$, or, $SO_2CH_3$;
R" is $CH_3$ or $C_2H_5$;
Y is $C_1$–$C_4$ alkoxy, phenoxy, phenoxy substituted by one or two halogen atoms, or, $OCH_2$—$CO$—$C(CH_3)_3$;
Z is $C_1$–$C_4$ alkyl, phenyl or R;
$NR_1R_2$ is $N(CH_3)_2$ $N(C_2H_5)_2$, morpholino, piperidino, hexamethylenimino, pyrrolidino.

This invention is also concerned with acid addition salts obtained from formula Ia compounds with acids.

Compounds of formulae I and Ia are useful as hypocholesterolemiant and hypolipidemiant agents.

11 Claims, No Drawings

ESTERS OF P-CARBONYLPHENOXY-ISOBUTYRIC ACIDS

This application is a divisional application of application Ser. No. 600,127 filed on July 29, 1975 now U.S. Pat. No. 4,058,552 which was a cip application of my previous U.S. patent application Ser. No. 326,188 of Jan. 24, 1973 now U.S. Pat. 3,907,792 which was itself a cip application of my U.S. patent application Ser. No. 8071 of Feb. 2, 1970 now U.S. Pat. No. 3,914,286.

This invention is concerned with esters of p-carbonylphenoxy-isobutyric acids.

This application is concerned with esters of the general formulae

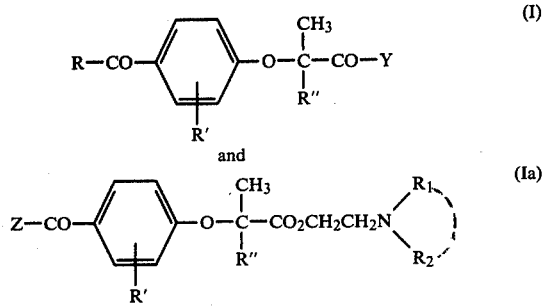

wherein
R is a phenyl group substituted by one or two halogen atoms;
R' is H, $CH_3$, $C_6H_5$, $SCH_3$, $OCH_3$, or, $SO_2CH_3$;
R" is $CH_3$ or $C_2H_5$
Y is $C_1$-$C_4$ alkoxy, phenoxy, phenoxy substituted by one or two halogen atoms, or $OCH_2O-CO-C(CH_3)_3$;
Z is $C_1$-$C_4$ alkyl, phenyl, or, R
$NR_1R_2$ is $N(CH_3)_2$ $N(C_2H_5)_2$, morpholino, piperidino, pyrrolidino, or, hexamethylenimino.

This application is also concerned with acid addition salts obtained from formula Ia compounds with inorganic and organic acids.

All the compounds of formula I and Ia have useful therapeutic properties. All of them are lipids and cholesterol reducing agents, moreover they act as normolipidemiant and hypocholesterolemiant agents. The acids (Y=OH) from which esters I and Ia are derived, induce gastric ulcers when administered by oral route, while their ester derivatives I and Ia do not develop gastric ulcers.

Some acids of the isobutyric type have been previously disclosed or suggested. AINSWORTH et al, J. Med. Chem., (1967), 10, 158-161 described two acids, namely the p-hexanoyl- and p-octanoylphenoxyisobutyric acids. NAKANISHI (U.S. Pat. No. 3,494,957) suggested the p-acetylphenoxy-isobutyric acid. CRAGOE (U.S. Pat. No. 3,704,314) suggested two acids, namely the p-butyrylphenoxy isobutyric acid and 2,3-dichloro-4-(2-methylenebutyryl-phenoxy-isobutyric acid, and an ester, namely the ethyl p-formylphenoxy-isobutyrate. On one hand these known acids present the disadvantage of inducing gastric ulcers, and on the other hand ethyl p-formylphenoxy-isobutyrate is less active than Clofibrate taken as a reference product. By halogen atoms I mean fluorine, chlorine, bromine and iodine atoms, the preferred halogen atom being chlorine. Thus, in the definition of R are included within the scope of this invention the 4-chlorophenyl, 3-chlorophenyl, 3,4-dichlorophenyl and 2,6-dichlorophenyl groups. The preferred R group is 4-chlorophenyl. The preferred R' and R" are respectively R'=H and R"=$CH_3$.

The esters of formula I are more active than their homologue compounds in which R is alkyl or cycloalkyl such as cyclohexyl. Moreover when the esters are p-carbonylphenoxy-isobutyric acid aminoethyl esters (i.e. compounds of the formula Ia), it is noticed that the presence of the $OCH_2CH_2NR_1R_2$ group enhances the hypocholesterolemiant and hypolipidemiant activities of the p-alkylcarbonyl compounds.

The preferred compound, that is to say the most useful therapeutically, is the isopropyl p-(4-chlorobenzoyl)-phenoxy-isobutyrate of formula I, which is coded as No. 178. Then comes the fumarate of β-azepino-ethyl p-(4-chlorobenzoyl)-phenoxy-isobutyrate of formula Ia, which is coded as No. 229.

The isobutyric acids (Y=OH) can be synthesized according to a method known per se. The methods I recommend are summed up by the following reaction schemes A and B, scheme B being the preferred one since it gives higher yields than A.

Scheme A

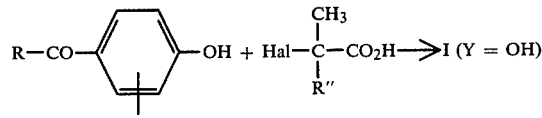

Scheme B

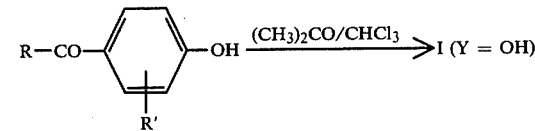

The esters I and Ia are obtained from the acids by a known process. For instance the esters may be prepared by esterification from the corresponding acids or by transesterification from another ester. For obtaining esters Ia the transesterification method is preferred.

Preparation I p-(4-Chlorobenzoyl)-phenoxy-isobutyric acid
(Code No. 153)

1 mole of 4-hydroxy-4'-chlorobenzophenone is dissolved in anhydrous acetone and then 5 moles of powdered sodium hydroxide is added. The corresponding sodium phevate precipitates. Refluxing is effected, and then, 1:5 mole of $CHCl_3$ diluted with anhydrous acetone is added and the resulting mixture is refluxed for 10 hours. After cooling, water is added, the acetone is evaporated, the aqueous phase is washed with ether and acidified and the organic phase is redissolved in ether and extracted into a solution of bicarbonate. The bicarbonate solution is then acidified to obtain the desired acid, having a melting point of 185° C., with a yield of 75%.

Preparation II

Isopropyl(p-4-chlorobenzoyl)-phenoxy-isobutyrate

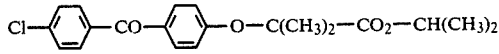

-continued
(Code No 178)

1 mole of the acid obtained in preparation I is converted into its acid chloride using thionyl chloride (2:5 moles). 1 mole of the acid chloride is then condensed with 1:05 mole of isopropyl alcohol in the presence of 0:98 mole of pyridine in an inert solvent such as benzene.

Since traces of $SO_2$ (which has a bad smell) may be obtained from the thionyl chloride; it is preferable to avoid this disadvantage by carrying out the esterification directly.

In table I, I have given examples of p-carbonyl-phenoxy-isobutyric acids which are used as intermediate compounds for the preparation of the esters according to this invention. They have been obtained according to reaction scheme A or B.

Tables II and III are respectively concerned with esters of formula I and esters of formula Ia. I have given in Table IV reference or comparison products. Moreover, p-alkylcarbonyl-phenoxy-isobutyric acid esters of table IV may be used for preparing the corresponding esters Ia by transesterification.

TABLE I

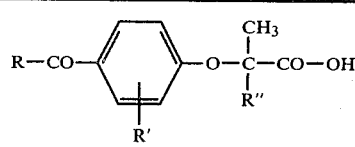

| Example | Code No. | R | R' | R'' | Melting or Boiling point |
|---|---|---|---|---|---|
| Ex 1 | 82 | $CH_3CH_2$ | H | $CH_3$ | F = 96° C. |
| Ex 2[a] | | $C_6H_5$ | H | $CH_3$ | |
| Ex 3[b] | | $CH_3(CH_2)_4$ | H | $CH_3$ | |
| Ex 4[b] | | $CH_3(CH_2)_6$ | H | $CH_3$ | |
| Ex 5[c] | | $CH_3$ | H | $CH_3$ | |
| Ex 6[a][d] | | $CH_3(CH_2)_2$ | H | $CH_3$ | F = 88° C. |
| Ex 7 | 153 | 4-Cl—$C_6H_4$ | H | $CH_3$ | F = 185° C. |
| Ex 8 | 198 | $CH_3(CH_2)_3$ | H | $CH_3$ | F = 62° C. |
| Ex 9 | 243 | $CH_3$ | 3-$CH_3$ | $CH_3$ | F = 98° C. |
| Ex 10 | — | $CH_3$ | 2-$C_6H_5$ | $CH_3$ | F = 106° C. |
| Ex 11 | 305 | 4-Cl—$C_6H_4$ | H | $C_2H_5$ | F = 140° C. |
| Ex 12 | 406 | 3-Cl—$C_6H_4$ | H | $CH_3$ | F = 121° C. |
| Ex 13 | 404 | 3,4-$Cl_2$—$C_6H_3$ | H | $CH_3$ | F = 155° C. |
| Ex 14 | 401 | 2,6-$Cl_2$—$C_6H_3$ | H | $CH_3$ | F = 196° C. |
| Ex 15 | 391 | cyclohexyl | H | $CH_3$ | F = 146° C. |
| Ex 16 | — | $CH_3$ | 3-$SO_2CH_3$ | $CH_3$ | — |

Notes
[a] disclosed in my previous U.S. Pat. application SN 8071
[b] disclosed by AINSWORTH
[c] suggested by NAKANISHI
[d] suggested by CRAGOE

TABLE II

R—CO—[ring, R']—O—C($CH_3$)($CH_3$)—CO—Y

| Example | Code No. | R | R' | Y | Melting or Boiling point |
|---|---|---|---|---|---|
| Ex 17 | 162 | 4-Cl—$C_6H_4$ | H | $OCH_3$ | F = 89° C. |
| Ex 18 | 163 | 4-Cl—$C_6H_4$ | H | $OC_2H_5$ | F = 79° C. |
| Ex 19 | 178 | 4-Cl—$C_6H_4$ | H | $OCH(CH_3)_2$ | F = 78° C. |
| Ex 20 | 217 | 4-Cl—$C_6H_4$ | H | p-$OC_6H_4Cl$ | F = 135° C. |
| Ex 21 | 403 | 3-Cl—$C_6H_4$ | H | $OCH(CH_3)_2$ | F = 79° C. |
| Ex 22 | 405 | 3,4-$Cl_2$—$C_6H_3$ | H | $OCH(CH_3)_2$ | F = 69° C. |
| Ex 23 | 402 | 2,6-$Cl_2$—$C_6H_3$ | H | $OCH(CH_3)_2$ | F = 115° C. |
| Ex 24 | 253 | 4-Cl—$C_6H_4$ | 3-$CH_3$ | $OCH(CH_3)_2$ | — |
| Ex 25 | 297 | 4-Cl—$C_6H_4$ | H | $OCH_2O$—$COC(CH_3)_3$ | F = 80° C. |

TABLE III

Z—CO—[ring, R']—O—C($CH_3$)($CH_3$)—CO—D $CH_2CH_2NR_1R_2$

| Example | Code No. | Z | R' | $OCH_2CH_2NR_1R_2$ | Melting or Boiling point |
|---|---|---|---|---|---|
| Ex 26 | 208 | $C_6H_5$ | H | $OCH_2CH_2N$(piperidine) fumarate | F = 100° C. |
| Ex 27 | 209 | $C_6H_5$ | H | $OCH_2CH_2N$(morpholine)O fumarate | F = 118° C. |

TABLE III-continued

Z—CO—C₆H₃(R')—O—C(CH₃)₂—CO—D CH₂CH₂NR₁R₂

| Example | Code No. | Z | R' | OCH₂CH₂NR₁R₂ | Melting or Boiling point |
|---|---|---|---|---|---|
| Ex 28 | 210 | CH₃ | H | OCH₂CH₂N(morpholino) | F = 134° C. |
| | | | | fumarate | |
| Ex 29 | 211 | C₆H₅ | H | OCH₂CH₂N(piperidino) | F = 115° C. |
| | | | | fumarate | |
| Ex 30 | 212 | C₆H₅ | H | OCH₂CH₂NEt₂ maleate | F = 62° C. |
| Ex 31 | 229 | 4-Cl—C₆H₄ | H | OCH₂CH₂N(piperidino) | F = 120° C. |
| | | | | fumarate | |
| Ex 32 | 230 | 4-Cl—C₆H₄ | H | OCH₂CH₂NEt₂ HCl | F = 104° C. |
| Ex 33 | 231 | 4-Cl—C₆H₄ | H | OCH₂CH₂N(piperidino) | F = 116° C. |
| | | | | fumarate | |
| Ex 34 | 232 | CH₃(CH₂)₃ | H | OCH₂CH₂NEt₂ HCl | F = 72° C. |
| Ex 35 | 233 | CH₃(CH₂)₃ | H | OCH₂CH₂N(piperidino) HCl | F = 118° C. |
| Ex 36 | 239 | 4-Cl—C₆H₅ | H | OCH₂CH₂N(morpholino) HCl | F = 145° C. |

TABLE IV

Reference, comparison and/or other intermediate compounds

R—CO—C₆H₃(R')—O—C(CH₃)₂—CO—Y

| Example | Code No. | R | R' | Y | Melting or Boiling point |
|---|---|---|---|---|---|
| Ex 37[c] | 180 | C₆H₅ | H | OCH₃ | F = 58° C. |
| Ex 38[a] | 186 | C₆H₅ | H | OC₂H₅ | F = 87° C. |
| Ex 39[a] | 190 | C₆H₅ | H | OCH(CH₃)₂ | F = 84° C. |
| Ex 40 | — | CH₃ | H | OC₂H₅ | $E_{0.03}$ = 120° C. |
| Ex 41 | — | CH₃CH₂CH₂ | H | OC₂H₅ | $E_{0.005}$ = 144° |
| Ex 42 | 140 | CH₃ | H | OCH₃ | F = 62° C. |
| Ex 43 | 188 | CH₃(CH₂)₃ | H | OCH₃ | $E_{0.05}$ = 147-9° |
| Ex 44 | 187 | CH₃(CH₂)₃ | H | OC₂H₅ | $E_{0.05}$ = 157-8° |
| Ex 45 | 189 | CH₃(CH₂)₃ | H | OCH(CH₃)₂ | $E_{0.05}$ = 156-7° |
| Ex 46 | — | H | H | OC₂H₅ | — |
| Ex 47 | 390 | cyclohexyl | H | OCH(CH₃)₂ | F = 148° C. |

TABLE IV-continued
Reference, comparison and/or other intermediate compounds

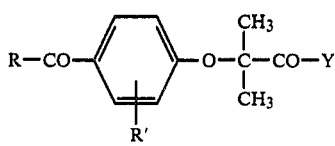

| Example | Code No. | R | R' | Y | Melting or Boiling point |
|---|---|---|---|---|---|
| Ex 48 | 238 | 4-Cl—$C_6H_5$ | H | $OCH_2$—[pyridine]·HCl | F = 144° C. |
| Ex 49 | 240 | $CH_3$ | 3-$CH_3$ | $OCH_3$ | $E_{0.05}$ = 132° C. |
| Ex 50 | 241 | $CH_3$ | 3-$CH_3$ | $OC_2H_5$ | $E_{0.05}$ = 136° C. |
| Ex 51 | 242 | $CH_3$ | 3-$CH_3$ | $OCH(CH_3)_2$ | $E_{0.05}$ = 139° C. |
| Ex 52 | — | $CH_3$ | 3-$SCH_3$ | $OCH(CH_3)_2$ | $E_1$ = 198° C. |
| Ex 53 | — | $CH_3$ | 3-$SO_2CH_3$ | $OCH(CH_3)_2$ | F = 86° C. |
| Ex 54 | — | $CH_3$ | 2-$C_6H_5$ | $OCH(CH_3)_2$ | F = 95° C. |

Notes
(a) and (c) see table I

The hypolipemiant and hypocholesterolemiant properties were exhibited in the rat. Each batch of rats (15 animals) is put on a fast at time t=0. A blood sample is taken at time t+15 hours, and then each product being tested is immediately administered orally. A new blood sample is taken at time t+39 hours. The variation (diminution) in the total amount of blood cholesterol and total amount of blood lipids is measured between t+15 hours and t+39 hours, and this variation is expressed in % in Table V in which the results obtained with the products according to this invention and reference products are shown.

The invention also relates to therapeutic compositions containing, in combination with a physiologically acceptable excipient, at least one compound of formula I or Ia or one of their non-toxic acid-addition salts.

TABLE V

| Example (Code No.) | dosage mg/kg | variation cholesterol % | variation lipids % |
|---|---|---|---|
| Ex 19 (178) | 50 | −30 | −32 |
| Ex 21 (403) | 100 | −21 | −18 |
| Ex 22 (405) | 100 | −10 | − 4 |
| Ex 23 (402) | 100 | − 9 | − 5 |
| Ex 27 (209) | 75 | −19 | −34 |
| Ex 31 (229) | 50 | −35 | −34 |
| Ex 36 (239) | 50 | −18 | −22 |
| Ex 24 (253) | 70 | −15 | −25 |
| Ex 28 (210) | 400 | −35 | −16 |
| Ex 35 (233) | 300 | −16 | −15 |
| Ex 38 (186) | 100 | −21 | −32 |
| Ex 39 (190) | 50 | −30 | −32 |
| Ex 40 | 300 | −28 | −34 |
| Ex 41 | 400 | −22 | −31 |
| Ex 47 (390) | 100 | N.S. | − 3 |

What is claimed is:

1. A novel ester of p-carbonylphenoxy-isobutyric acid selected from the group consisting of
   (a) compounds of the formula $$Z-CO-\underset{R'}{\underset{|}{\bigcirc}}-O-\underset{R''}{\overset{CH_3}{\underset{|}{C}}}-CO_2-CH_2CH_2N\underset{R_2}{\overset{R_1}{\diagdown}}$$

wherein
R' is H, $CH_3$, $C_6H_5$, $SCH_3$, $OCH_3$, or $SO_2CH_3$;
R" is $CH_3$ or $C_2H_5$;
Z is a phenyl group substituted by one halogen atom and
$NR_1R_2$ is $N(CH_3)_2$, $N(C_2H_5)_2$, morpholino, piperidino, hexamethylenimino or pyrrolidino, and
   (b) non-toxic acid addition salt thereof.

2. A novel ester of p-carbonylphenoxy-isobutyric acid having the formula $$Z-CO-\bigcirc-O-\overset{CH_3}{\underset{\underset{CH_3}{|}}{C}}-CO_2-CH_2CH_2N\overset{R_1}{\diagdown}_{R_2}$$

wherein Z is a 4-chlorophenyl group, and $NR_1R_2$ is $N(C_2H_5)_2$, morpholino, piperidino or hexamethylenimino; and its non-toxic acid addition salts.

3. A novel ester of p-carbonylphenoxy-isobutyric-acid having the formula $$Z-CO-\bigcirc-O-\overset{CH_3}{\underset{\underset{CH_3}{|}}{C}}-CO_2-CH_2CH_2N\overset{R_1}{\diagdown}_{R_2}$$

wherein Z is $C_1$-$C_4$ alkyl, phenyl or chlorophenyl and $NR_1R_2$ is a hexamethylenimino group and non-toxic acid addition salts thereof.

4. A novel ester according to claim 1 in which $NR_1R_2$ is a hexamethylenimino group.

5. β-hexamethyleniminoethyl-p-(4-chlorobenzoyl)-phenoxy-isobutyrate and its non-toxic acid addition salts.

6. A novel ester of the formula

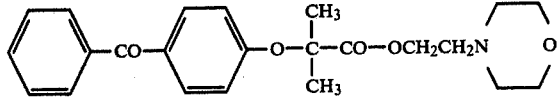

and nontoxic acid addition salts thereof.

7. A novel ester of the formula

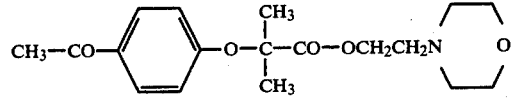

and nontoxic acid addition salts thereof.

8. A novel ester of the formula

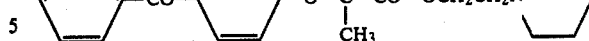

and nontoxic acid addition salts thereof.

9. A novel ester of the formula

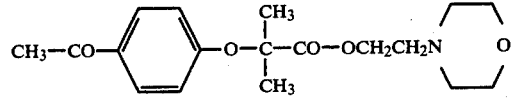

and nontoxic acid addition salts thereof.

10. A therapeutic composition useful for treating patients in order to reduce their blood cholesterol and lipids content, which comprises, in association with a pharmaceutically acceptable excipient, a therapeutically effective amount of at least a compound according to any one of claims 1, 2, 3 or 6–11.

11. A novel ester of the formula

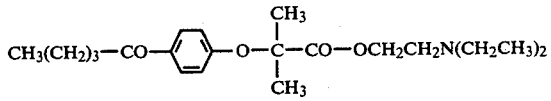

and nontoxic acid addition salts thereof.

* * * * *